(12) United States Patent
Cude

(10) Patent No.: US 8,986,226 B2
(45) Date of Patent: Mar. 24, 2015

(54) GUIDEWIRE POSITIONING TOOL

(71) Applicant: Coeur, Inc.

(72) Inventor: J. Michael Cude, College Grove, TN (US)

(73) Assignee: Coeur, Inc., Lebanon, TN (US)

( * ) Notice: Subject to any disclaimer, the term of this patent is extended or adjusted under 35 U.S.C. 154(b) by 0 days.

(21) Appl. No.: 13/646,436

(22) Filed: Oct. 5, 2012

(65) Prior Publication Data
US 2013/0190731 A1 Jul. 25, 2013

Related U.S. Application Data

(60) Provisional application No. 61/543,641, filed on Oct. 5, 2011, provisional application No. 61/701,950, filed on Sep. 17, 2012.

(51) Int. Cl.
A61M 25/00 (2006.01)
A61M 25/09 (2006.01)
A61B 17/00 (2006.01)

(52) U.S. Cl.
CPC ...... *A61M 25/09041* (2013.01); *A61B 2017/00469* (2013.01)
USPC .......................................................... 600/585

(58) Field of Classification Search
CPC .................. A61M 25/09041; A61M 25/0905; A61M 2025/09116
USPC ........ 600/433, 434, 585; 604/164.13, 166.01, 604/528
See application file for complete search history.

(56) References Cited

U.S. PATENT DOCUMENTS

| 5,161,534 | A  | * | 11/1992 | Berthiaume ................. 600/434 |
| 7,959,584 | B2 |   | 6/2011  | Esksuri et al. |
| 8,025,629 | B2 | * | 9/2011  | Shelton ........................ 600/585 |
| 8,372,057 | B2 |   | 2/2013  | Cude |
| 2003/0225418 | A1 |   | 12/2003 | Esksuri et al. |
| 2005/0240120 | A1 | * | 10/2005 | Modesitt ....................... 600/585 |
| 2008/0014699 | A1 |   | 1/2008  | Torek et al. |
| 2010/0016792 | A1 |   | 1/2010  | Hirszowicz |
| 2010/0094260 | A1 |   | 4/2010  | Cude |

FOREIGN PATENT DOCUMENTS

| JP | 2005527332 A | 9/2005 |
| JP | 2008149124 A | 7/2008 |
| WO | 2004096338 A1 | 11/2004 |

* cited by examiner

Primary Examiner — Max Hindenburg
Assistant Examiner — Jonathan M Foreman
(74) Attorney, Agent, or Firm — Hahn Loeser & Parks LLP

(57) ABSTRACT

A guidewire positioning tool includes a sheath having a body bore extending axially through a length of the sheath with a radially extending body slot configured to receive a guidewire. A collet portion extends laterally from the sheath and has collet arms and interstitial spaces with a collet bore extending therethrough. The collet bore has a collet slot extending radially from the collet bore configured to receive a guidewire. The collet arms have threads located on the exterior of the collet arms. A clamp nut is positioned over the collet portion and configured to threadably engage the threads. A retainer is rotatably attached to an end of the sheath opposite from the collet portion. The retainer has a retainer bore extending axially therethrough. The retainer has a retainer slot extending radially from the retainer bore configured to receive a guidewire.

20 Claims, 21 Drawing Sheets

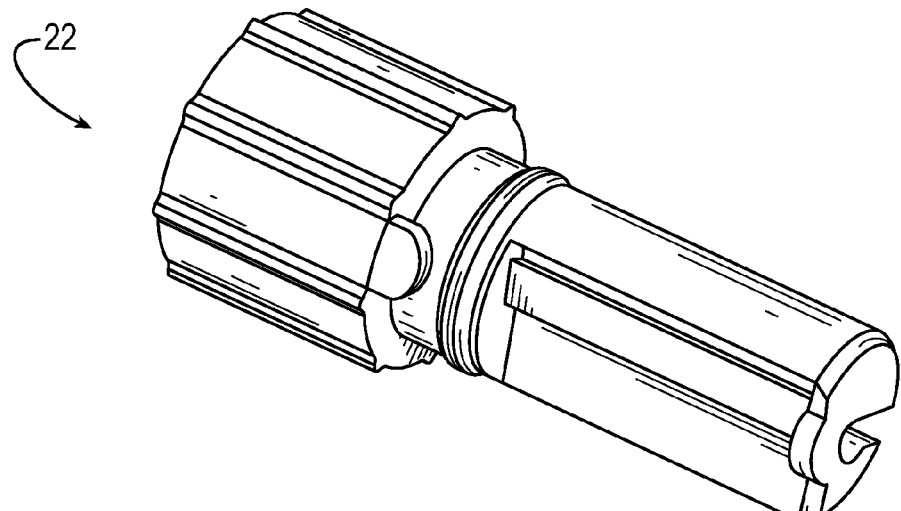
FIG. 3A₁
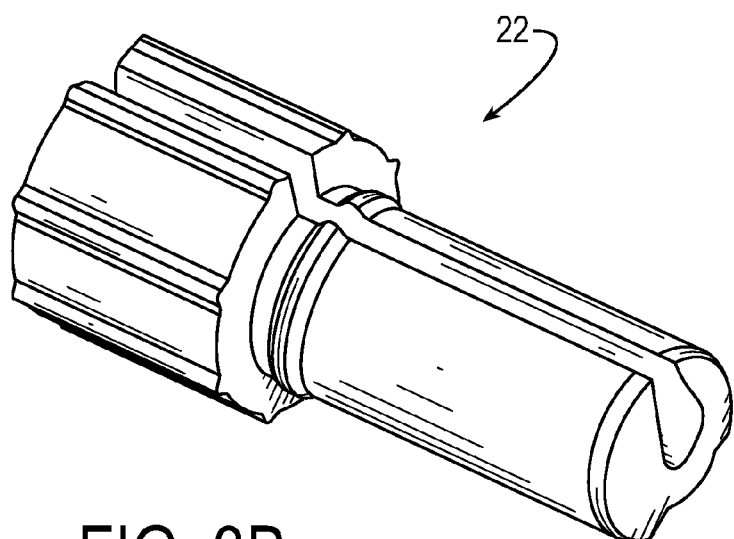
FIG. 3B₁

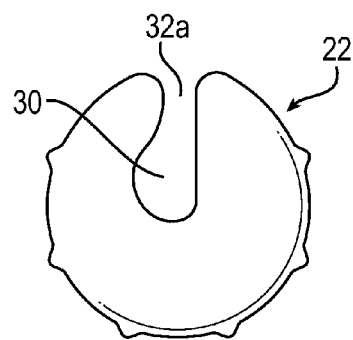
FIG. 3C₁
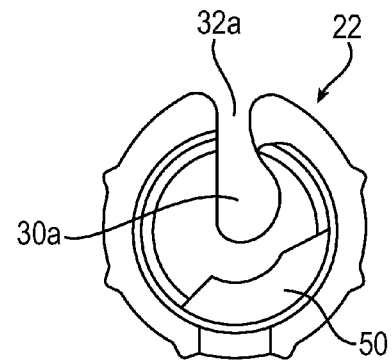
FIG. 3C₂
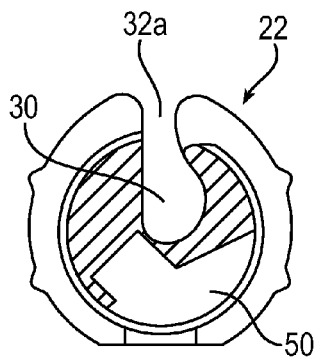
FIG. 3E

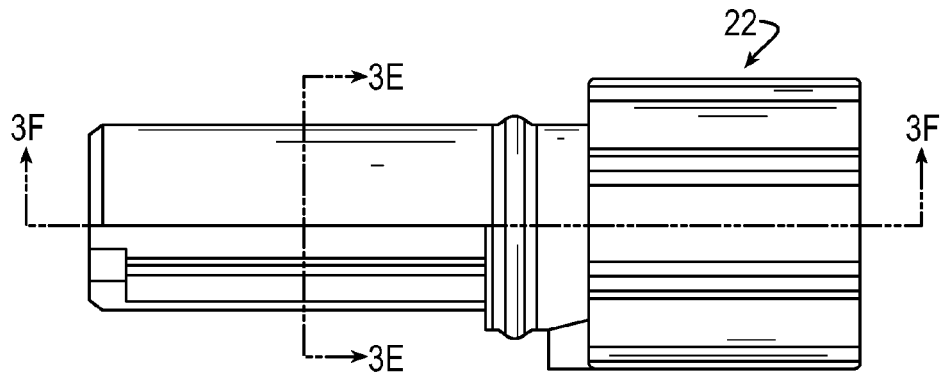
FIG. 3D₁
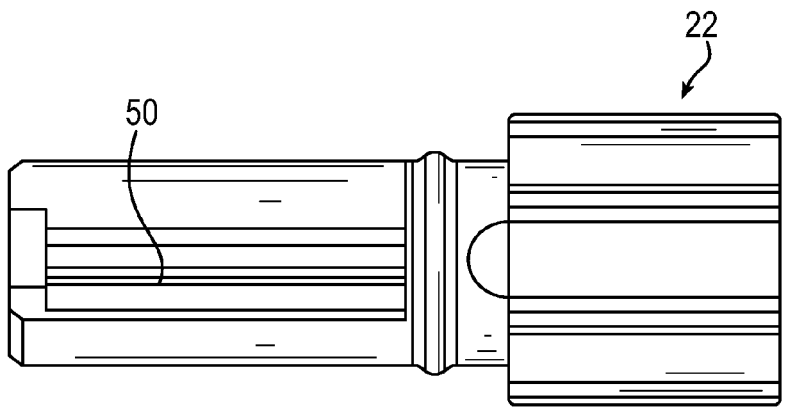
FIG. 3D₂
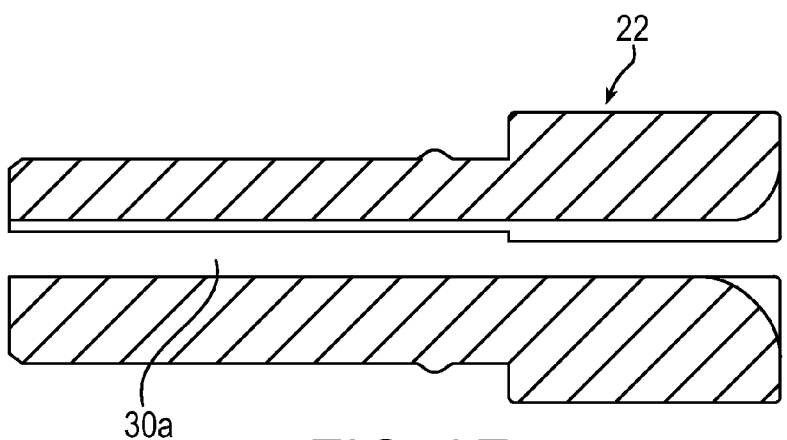
FIG. 3F

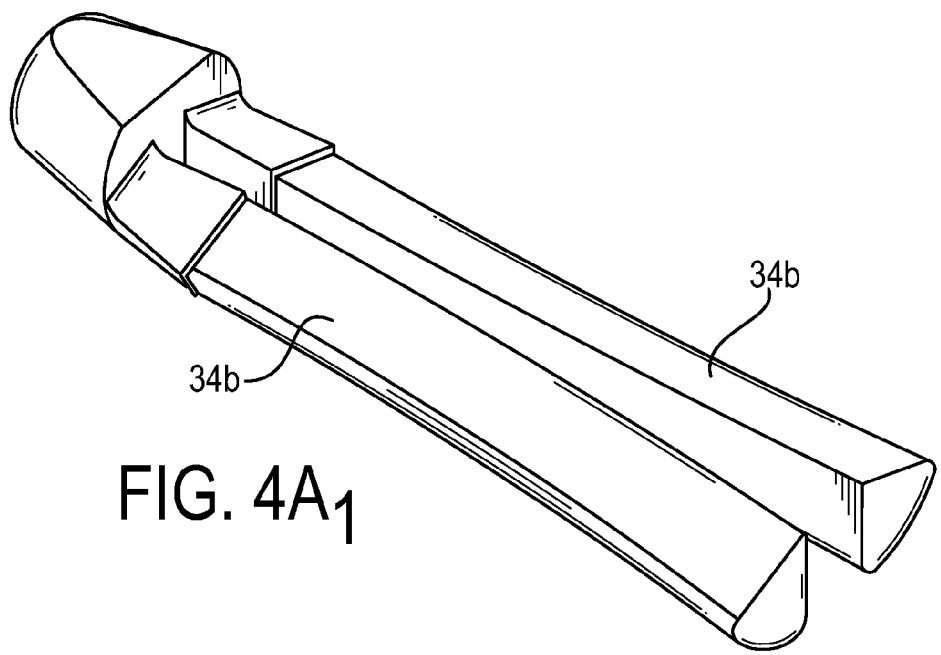
FIG. 4A₁
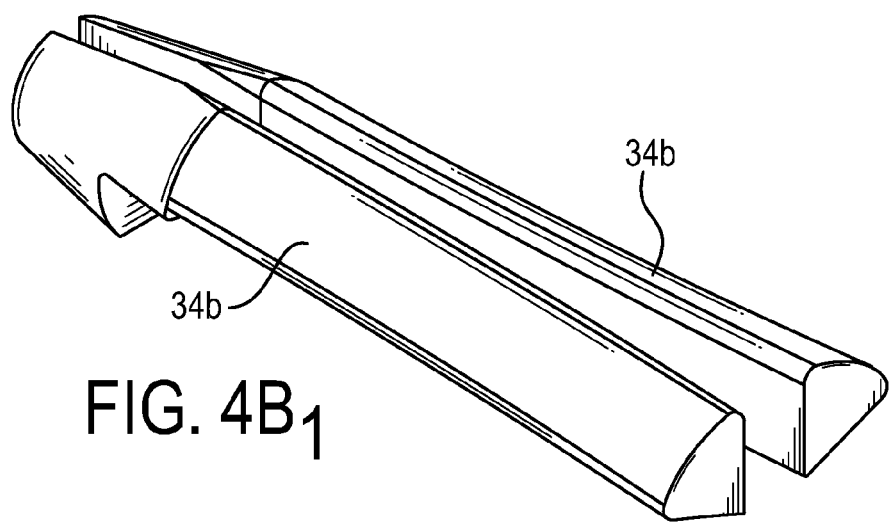
FIG. 4B₁

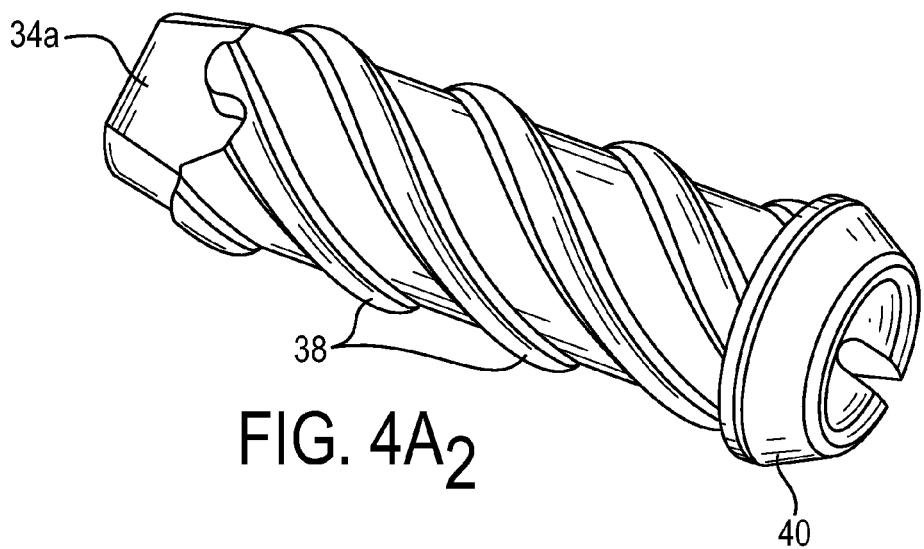
FIG. 4A₂
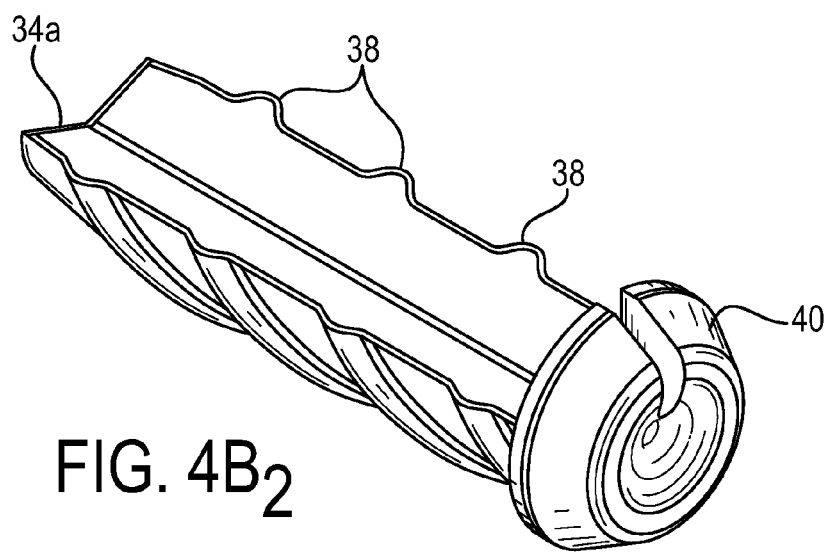
FIG. 4B₂

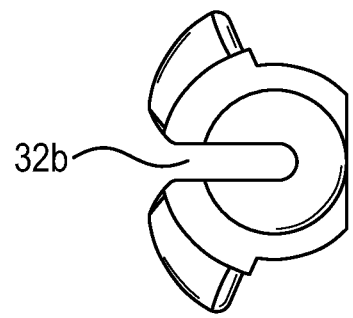
FIG. 4C₁
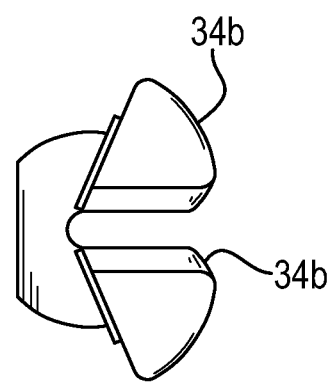
FIG. 4D₁

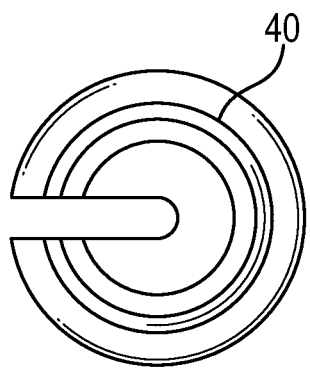
FIG. 4C$_2$
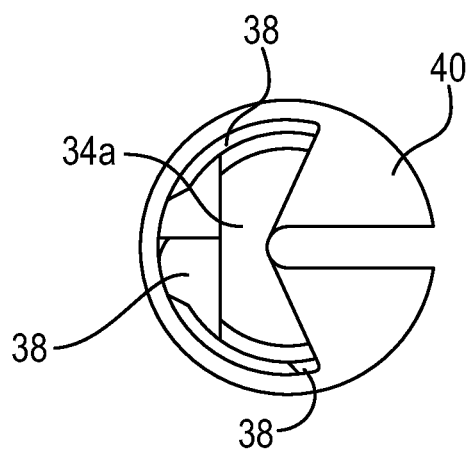
FIG. 4D$_2$

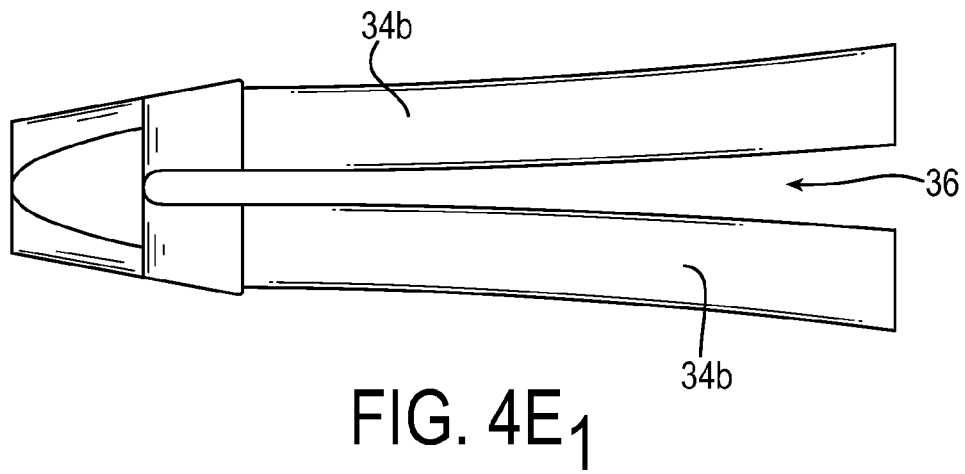
FIG. 4E₁
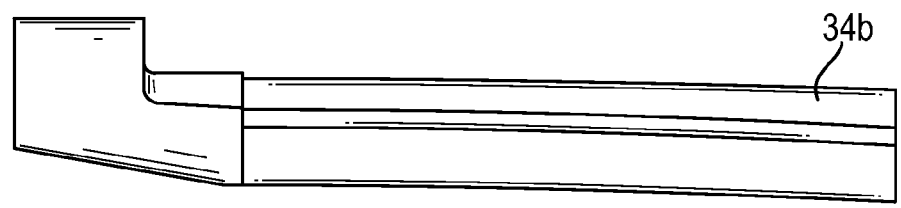
FIG. 4E₂

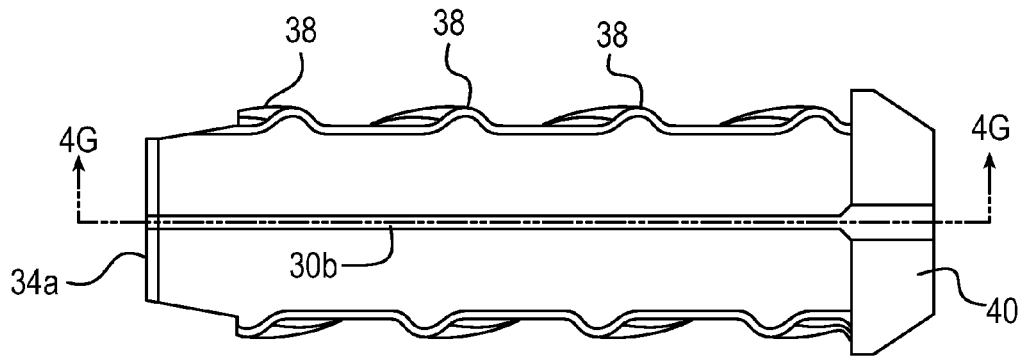
FIG. 4F₁
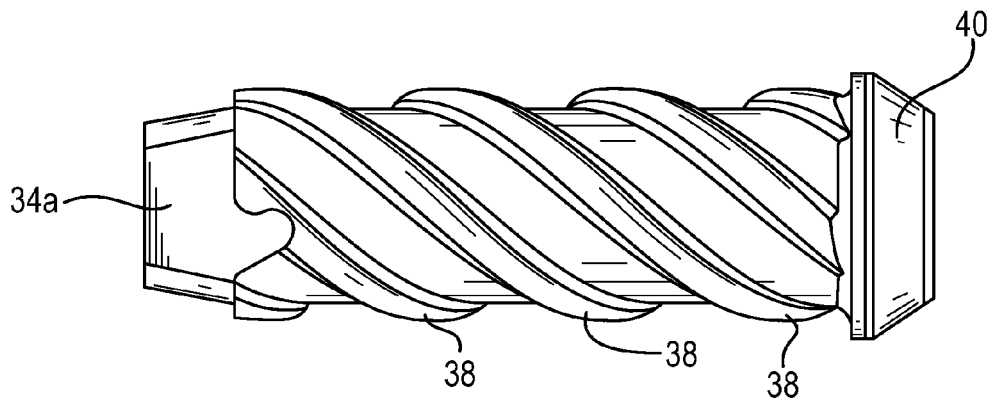
FIG. 4F₂
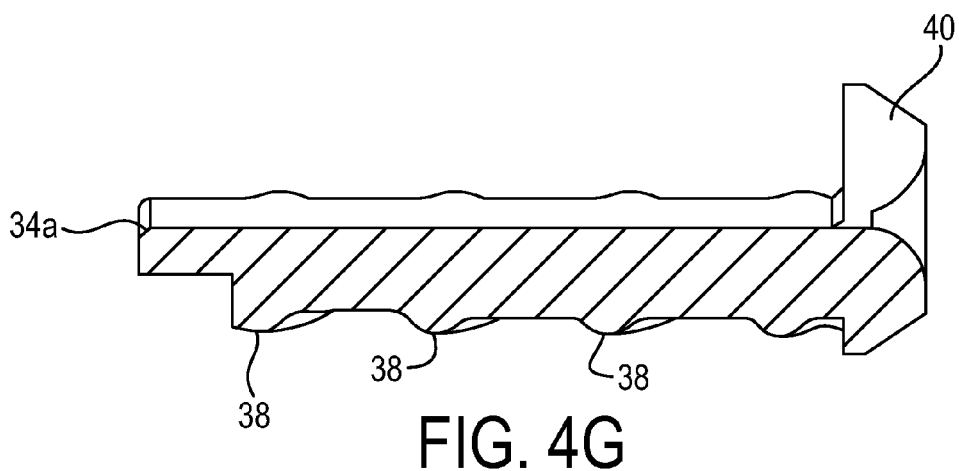
FIG. 4G

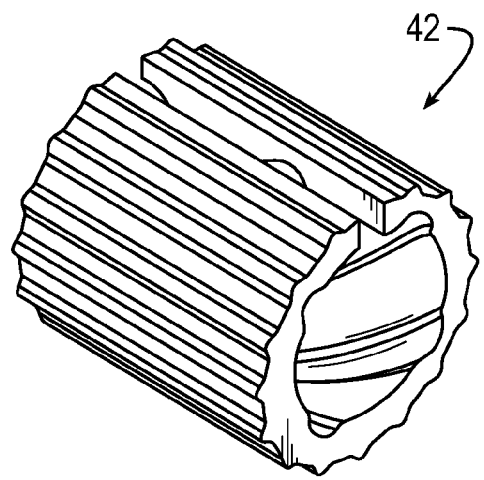
FIG. 6A₁
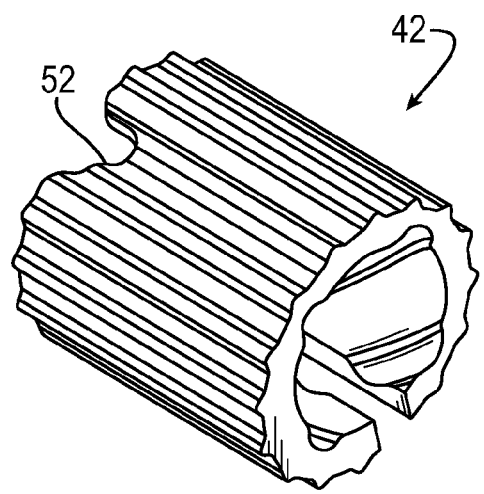
FIG. 6A₂

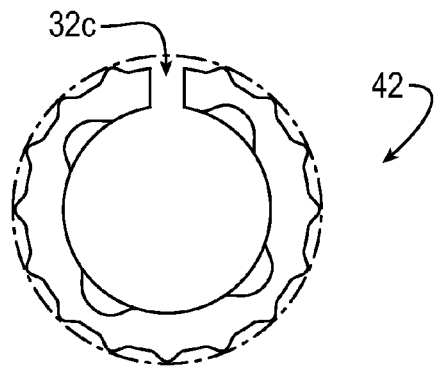
FIG. 6B₁
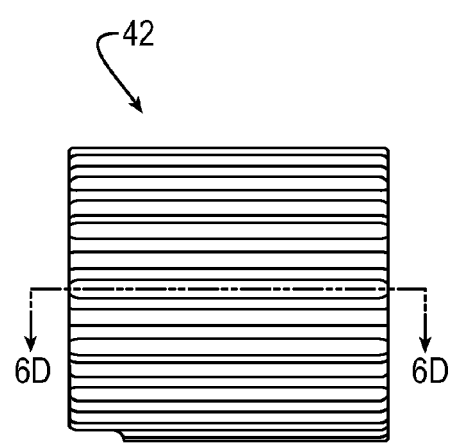
FIG. 6C
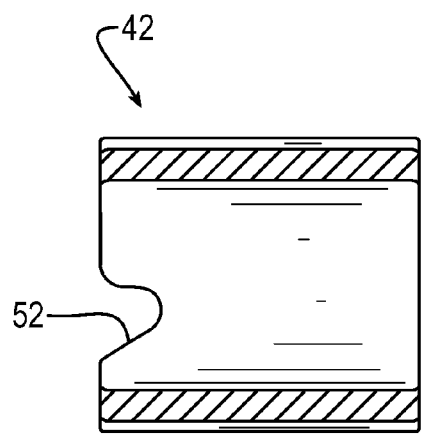
FIG. 6D

GUIDEWIRE POSITIONING TOOL

CROSS-REFERENCE TO RELATED APPLICATIONS

This application claims the benefit of U.S. Provisional Application No. 61/543,641, filed Oct. 5, 2011, and U.S. Provisional Application No. 61/701,950, filed Sep. 17, 2012, the disclosures of which are both incorporated herein by reference.

BACKGROUND

Medical guidewires are devices that may be used to assist in the positioning of catheters, stents, and other medical devices in the circulatory, lymphatic, and other systems. Typically, a user will insert the guidewire percutaneously, and proceed to feed the guidewire through the vasculature system. The user may navigate the guidewire through branches in the vasculature. In one application, when the guidewire reaches a desired location, a catheter, stent, or other device may be advanced over the path defined by the guidewire and subsequently placed at the desired location.

The width of a guidewire is generally correlated with the width of the vasculature system of intended use. For example, diameters from 0.010" to 0.038" are common guidewire sizes in the medical field. The length of a guidewire may be limited by the type of procedure and/or the desired location within the vasculature. Lengths ranging from 50 cm to 450 cm are common. As a result, guidewires are often long and slender and it depends upon the skill of a particular user to manipulate and advance the guidewire in use.

SUMMARY

A guidewire positioning tool includes a sheath having a bore extending axially through a length of the sheath. The bore has a slot extending radially from the bore. The bore and the slot are configured to receive a guidewire. A collet portion extends laterally from the sheath. The collet has collet arms and interstitial spaces. A bore extends axially through a length of the collet portion. The bore has a slot extending radially from the bore. The bore and the slot are configured to receive a guidewire. The collet arms have threads located on the exterior of the collet arms. A clamp nut is positioned over the collet portion and configured to threadably engage the threads. A retainer is rotatably attached to an end of the sheath opposite from the collet portion. The retainer has a bore extending axially through a length of the retainer. The bore has a slot extending radially from the bore. The bore and the slot are configured to receive a guidewire.

In at least one embodiment, the tool may include visual or mechanical locked and/or unlocked indicators.

In at least one embodiment, the sheath may include a radially positioned aperture to allow for fluid communication between the exterior of the sheath and the bore of the sheath. Also, the retainer may include a pocket for receiving fluid. In an embodiment where both are present, the aperture and the pocket may be aligned for fluid communication when in an open position, with the aperture and the pocket not aligned for fluid communication when in a locked position.

In at least one embodiment, one of the retainer and the sheath or collet includes a protrusion and the other of the retainer and the sheath or collet includes a recess. In one example, the protrusion and the recess cooperate to act as a tongue and groove arrangement to limit the movement of the retainer relative to the sheath when transitioning between a locked and an open position relative to the sheath. In another example, the protrusion and the recess cooperate to act as a detent mechanism to hold the retainer in one of a locked or open position relative to the sheath. In any case, the one of the protrusion and the recess included with the retainer may be formed upon an interior end of the retainer and the other of the protrusion and the recessed included with the sheath or collet may be formed on an interior portion of the sheath or collet.

In at least one embodiment, the clamp nut includes a visual indicator to indicate position of the clamp nut relative to the collet portion. In one example, the visual indicator may be a change in color about the circumference of the clamp nut. In another example, the visual indicator may be a marker on the exterior of the clamp nut. It is contemplated that the marker may align with the slot of the collet portion when in a locked position and not align with the slot of the collet portion when in an open position, although such is not required.

In at least one embodiment, one of the clamp nut and the sheath includes a protrusion and the other of the clamp nut and the sheath includes a recess where the protrusion and recess cooperate to act as a tongue and groove arrangement to limit the movement of the clamp nut relative to the sheath when transitioning between a locked and an open position relative to the sheath.

In at least one embodiment, one of the clamp nut and the sheath includes a protrusion and the other of the clamp nut and the sheath includes a recess where the protrusion and the recess cooperate to act as a detent mechanism to hold the clamp nut in one of a locked or open position relative to the sheath.

In one method of use of the tool, a user may manipulate a guidewire through vasculature with the tool retained on the guidewire. The user may grip the tool and apply force to the guidewire. In one operation the tool may be laterally mounted on a guidewire during a procedure without needing to insert the guidewire longitudinally. As such, the tool may be unmounted and a different tool may be mounted if so desired. Additionally, the user may optionally manipulate the tool with a single hand.

Various aspects will become apparent to those skilled in the art from the following detailed description and the accompanying drawings.

BRIEF DESCRIPTION OF THE DRAWINGS

FIGS. 3*a*1, *b*1, *c*1, *c*2, *d*1, *d*2, *e* and *f* are a perspective view, a rotated perspective view, a first end view, a second end view, a side view, a rotated side view, a cross-sectional view taken along line E-E, and a cross-sectional view taken along line F-F, respectively, of another embodiment of the retainer of the guidewire positioning tool of FIG. 1.

FIGS. 4*a*1, *b*1, *c*1, *d*1, *e*1, and *e*2, are a perspective view, a rotated perspective view, a first end view, a second end view, a side view, and a rotated side view, respectively, of the upper fingers of another embodiment of the collet of the guidewire positioning tool of FIG. 1.

FIGS. 4a2, b2, c2, d2, f1, f2, and g, are a perspective view, a rotated perspective view, a first end view, a second end view, a top view, a bottom view, and a cross-sectional view taken along line G-G, respectively, of the lower fingers with cap, of another embodiment of the collet of the guidewire positioning tool of FIG. 1.

FIGS. 6a1, a2, b1, c, and d, are a perspective view, a rotated perspective view, an end view, a side view, and a cross sectional view taken along line D-D, respectively, of another embodiment of the clamp nut of the guidewire positioning tool of FIG. 1.

DETAILED DESCRIPTION

Figure 1:
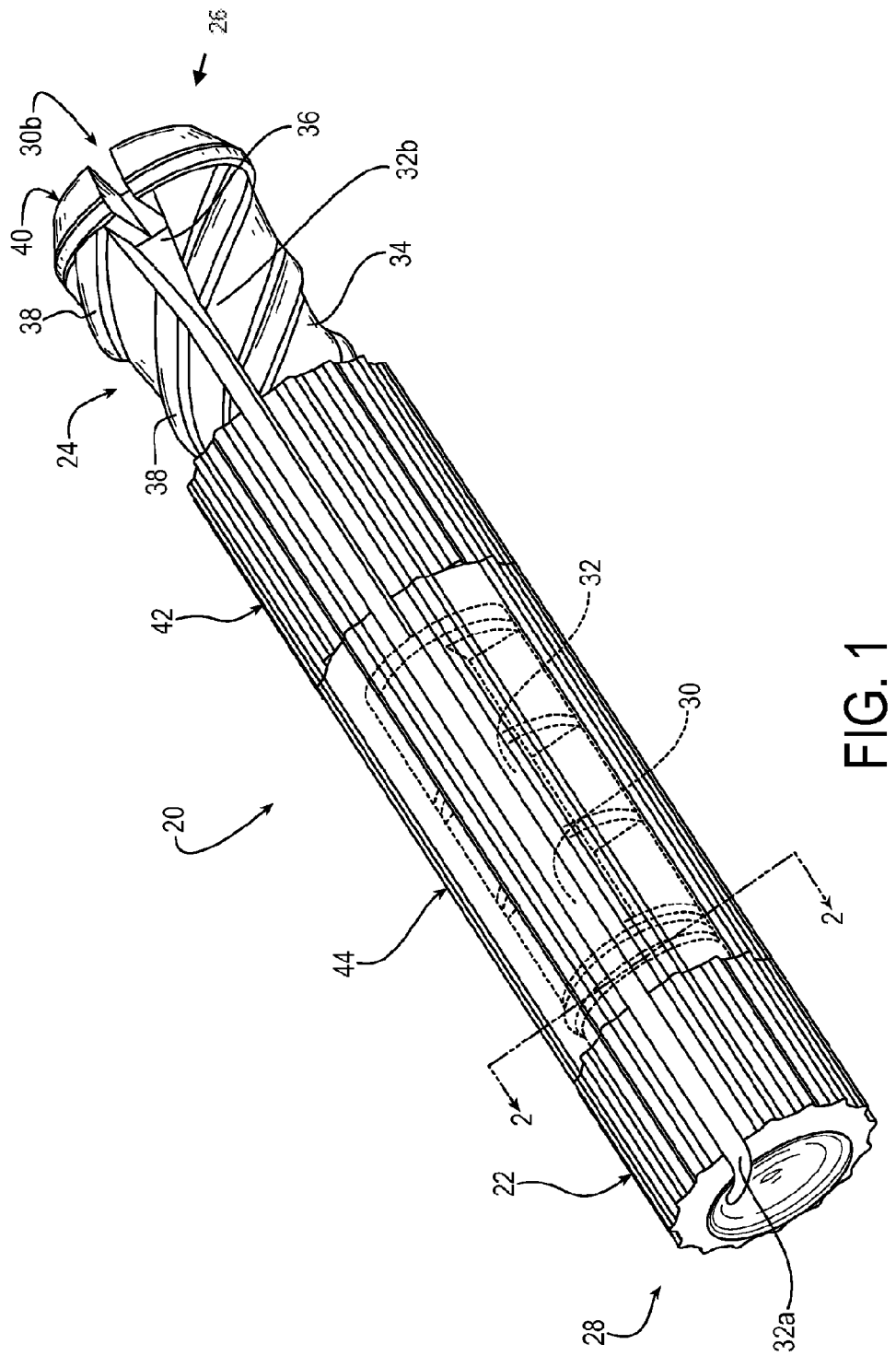
FIG. 1 is a side perspective view of a guidewire positioning tool.

There is shown in FIG. 1 a guidewire positioning tool that has a body 20 with a retainer 22 and a collet 24. The body 20 has a proximal end 26 and a distal end 28. In the illustrated embodiment, the body 20 is generally cylindrically shaped, although the body may be shaped otherwise. The body 20 includes a sheath 44 which has a bore 30 extending axially through its length. Extending radially from the bore 30 is a slot 32 configured to receive a guidewire. The slot 32 extends laterally along the entire length of the sheath 44.

The retainer 22 has a bore 30a extending axially through its length. Extending radially from the bore 30a is a slot 32a configured to receive a guidewire. As illustrated, the bore 30a and the slot 32a are sized similarly to the bore 30 and slot 32 of the sheath 44, although such is not required. In at least one embodiment, the retainer 22 is configured for limited rotation, such as 60, 90, or 120 degrees or any other desired amount, relative to the sheath 44. Alternatively, the retainer 22 may be configured to rotate freely about the sheath 44. In an unlocked, or open, position, the slot 32a is aligned with the slot 32 to facilitate placement of the guidewire positioning tool on a guidewire longitudinally. In a closed, or locked, position, the retainer 22 is rotated such that the slot 32a is unaligned with the slot 32 and thus prevents displacement of the guidewire positioning tool and an associated guidewire in a longitudinal fashion.

Figure 3A:
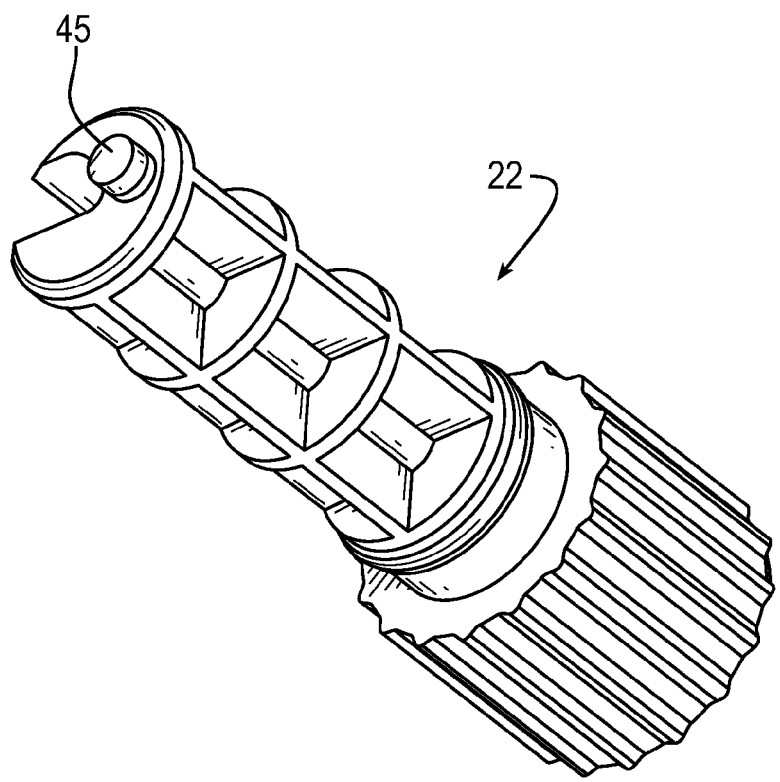
FIGS. 3*a, b,* and *c* are a perspective view, a rotated perspective view and an end view, respectively, of one embodiment of the retainer of the guidewire positioning tool of FIG. 1.
Figure 3B:
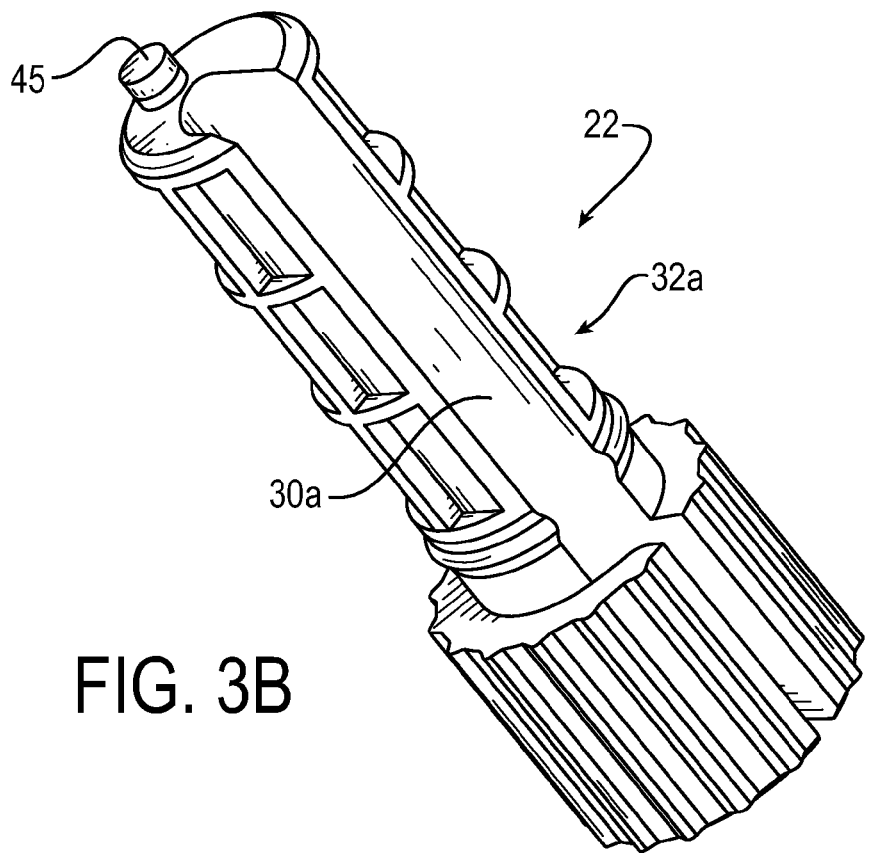
Figure 3C:
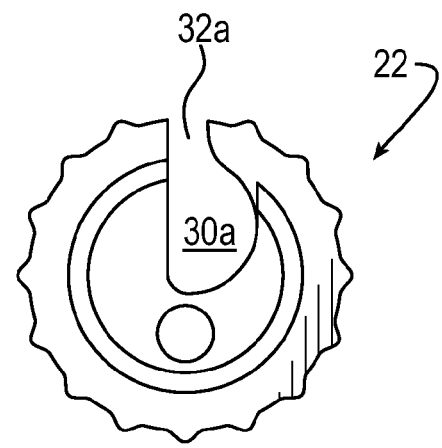

As best shown in FIGS. 3a1, b1, c1, c2, d1, d2, e and f, the retainer 22 may include a pocket 50 for the placement and/or retention of fluid, such as fluid used to lubricate. The fluid may be placed in the pocket 50 before the assembly of the body 20 or after assembly as will be further described below.

The collet 24 has a bore 30b extending axially along its length. Extending radially from the bore 30b is a slot 32b that is configured to receive a guidewire. In the illustrated embodiment, the bore 30b and the slot 32b are sized similarly to the bores 30 and 30a and to the slots 32 and 32a of the sheath 44 and retainer 22, respectively, although such is not required.

The collet 24 is includes a number collet arms 34, such as two, three, four, or more or any suitable number. Between the collet arms 34 is an interstitial space 36. Interstitial spaces 36 are preferably narrower proximal to the sheath 44 than they are distal to the sheath 44. One of the interstitial spaces 36 may be the slot 32b, configured to receive a guidewire. However, the remaining interstitial spaces 36 may not necessarily be similarly sized. The portion of the collet arms 34 exterior to the bore 30b feature threads 38. Distal from the sheath 44, the collet 24 has a cap 40.

Figure 2:
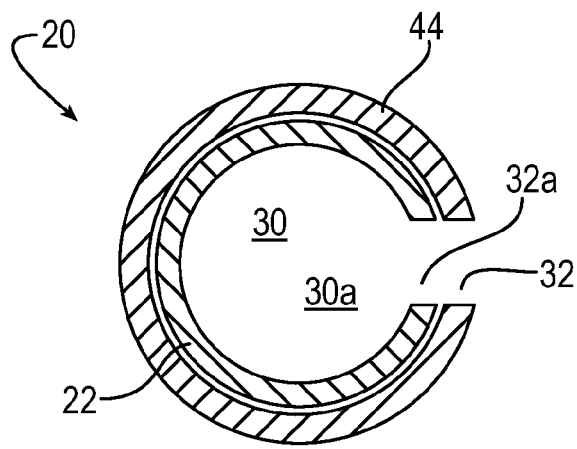
FIG. 2 is a cross-section of the body of the guidewire positioning tool of FIG. 1 taken along line 2-2.
Figure 4A:
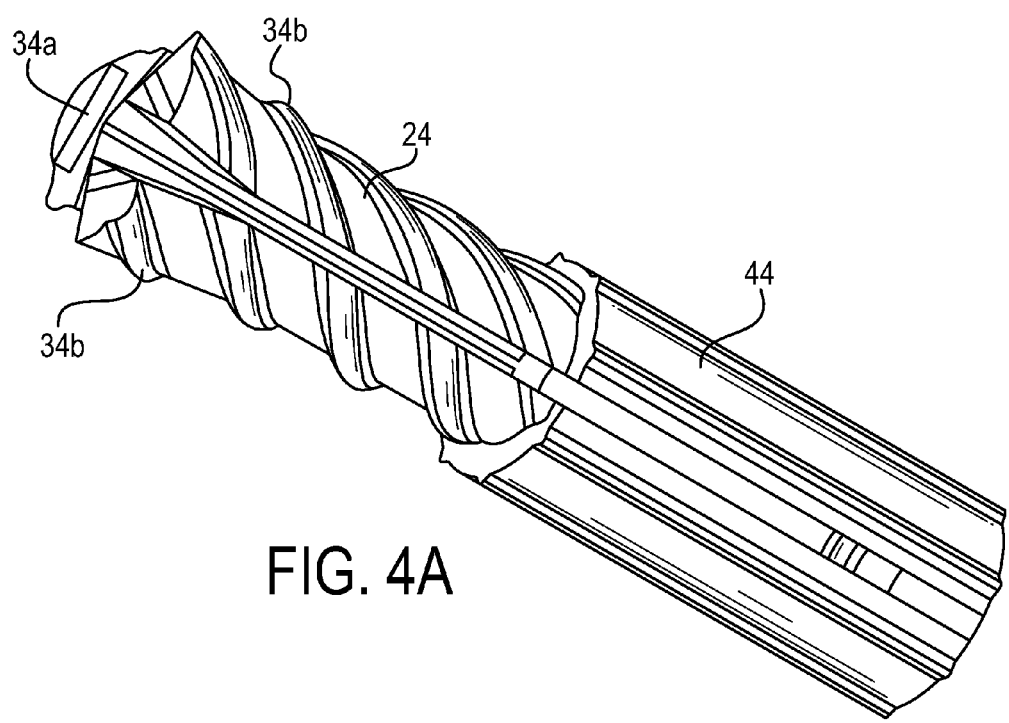
FIGS. 4*a, b, c,* and *d* are a perspective view, a rotated perspective view, and a first end view, respectively, of one embodiment of the collet of the guidewire positioning tool of FIG. 1.
Figure 4B:
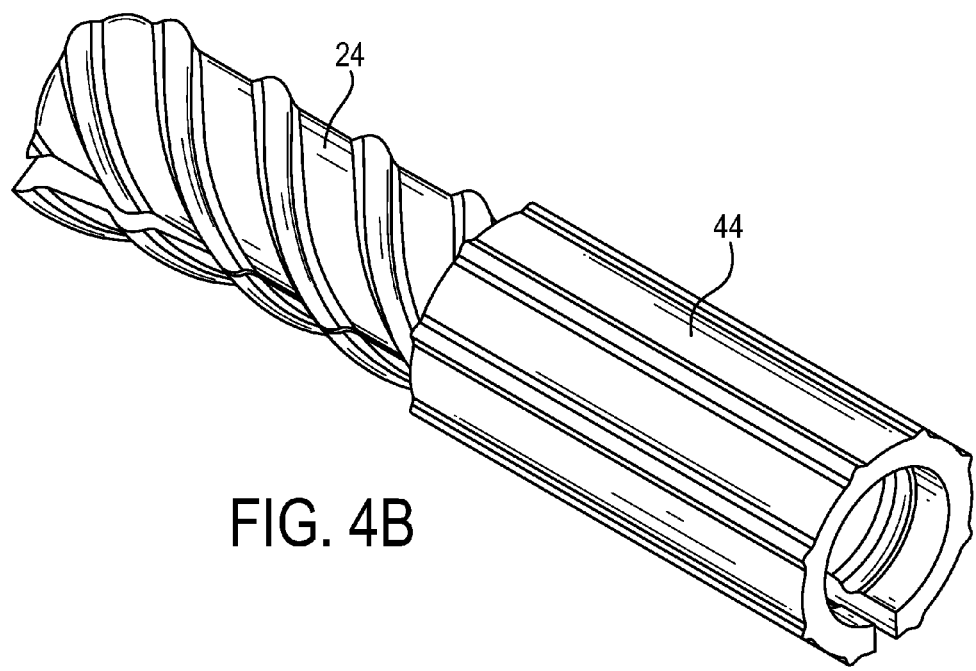
Figure 4C:
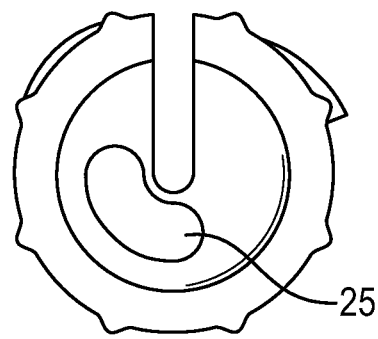
Figure 4D:
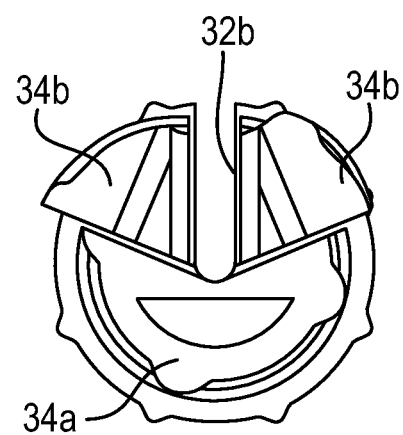

As best shown in FIGS. 4a1, b1, c1, d1, e1, and e2, and FIGS. 4a2, b2, c2, d2, f1, f2, and g, the collet 24 may be formed from a portion of upper collet arms joined with a portion lower collet arms including the cap 40.

Figure 6A:
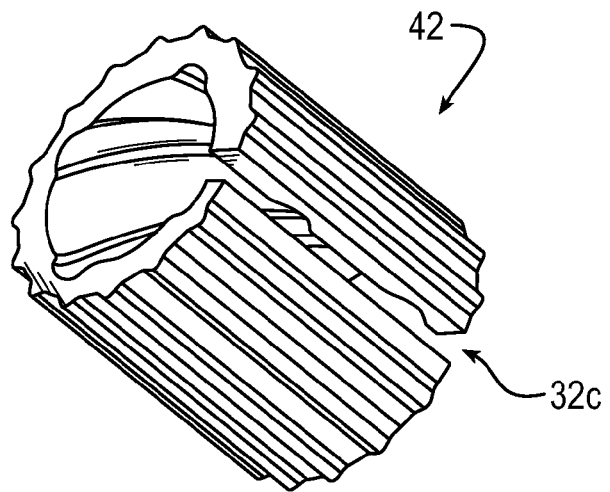
FIGS. 6a and b are a perspective view and an end view, respectively, of one embodiment of the clamp nut of the guidewire positioning tool of FIG. 1.
Figure 6B:
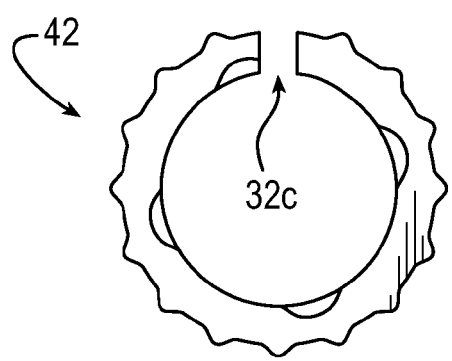

A clamp nut 42, see FIGS. 6a, and 6b, is disposed on the collet 24 and configured to engage the threads 38. The clamp nut 42 also has a slot 32c. In the unlocked, or open, position, the clamp nut is positioned on the collet 24 proximal to the sheath 44, and with its slot 32c aligned with the slot 32. In one embodiment, in the closed, or locked, position, the clamp nut 42 is positioned on the collet 24 proximal to the cap 40, and with its slot 32c unaligned with the slot 32.

In one embodiment, the helical pitch of the threads 38 limits the rotation of the clamp nut 42 to one half turn, or 180°, about the collet 24. In other embodiments, the helical pitch of the threads 38 may limit the rotation of the clamp nut 42 to one quarter turn, or 90°, about the collet 24. In still other embodiments, the helical pitch of the threads 38 may limit the rotation of the clamp nut 42 to one full turn, or 360°, about the collet 24. Finally, in still other embodiments, the helical pitch of the threads 38 may limit the rotation of the clamp nut 42 to two or more full turns or any other desired amount.

In any case, rotation of the clamp nut 42 may cease where the collet 24 abuts the cap 40, thus using the cap 40 as stop, although such is not required. However, in other embodiments, rotation of the clamp nut 42 may cease at any desired point along the collet 24, for example due to change in diameter of the collet 24.

The helical pitch of the threads 38 may correspond to the anticipated size of the guidewire. In some embodiments, the helical pitch will be small to accommodate a small guidewire. In other embodiments, the helical pitch will be large to accommodate a large guidewire. Finally, in still other embodiments, the helical pitch may not be correlated to the anticipated size of the guidewire. The threads 38 may have a right-handed pitch in some embodiments and a left-handed pitch in others.

In embodiments where the clamp nut 42 abuts the cap 40 in the closed, or locked, position and where the clamp nut 42 abuts the sheath 44 in the unlocked, or open, position, the relative position of the clamp nut 42 may provide an easy visualized locked and unlocked indicator. In some embodiments the clamp nut 42 may be a different color than the sheath 44 or the cap 40 to further make the locked and unlocked indications easy to visualize. Further, the color of the clamp nut 42 may vary about the circumference of the clamp nut 42 such that the color relative to a relatively stationary place on the body 20, such at the slot 30 of the sheath 44 or the slot of the cap 40, may indicate the position of the clamp nut 42.

Figure 7A:
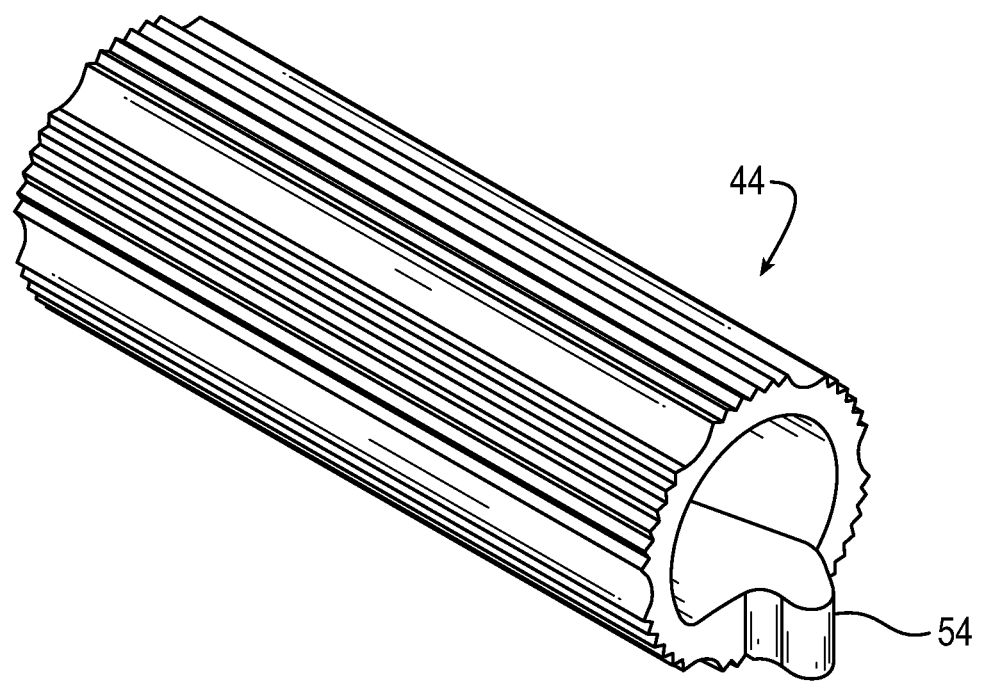
FIGS. 7a, b, c, d, e, and f are a perspective view, a first end view, an enlarged end view at C, a second end view, a side view, and a cross-sectional view taken along line F-F, respectively, of one embodiment of the sheath of the guidewire positioning tool of FIG. 1.
Figure 7B:
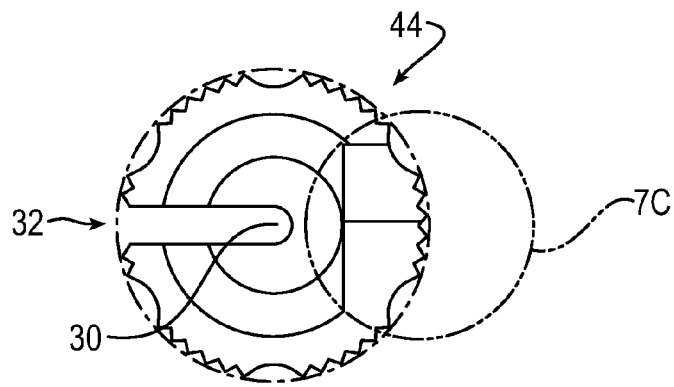
Figure 7C:
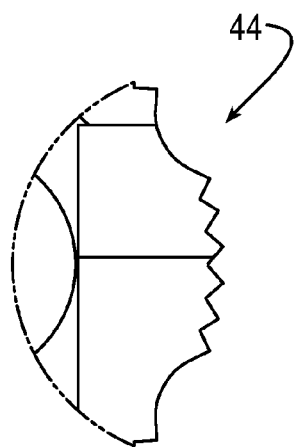
Figure 7D:
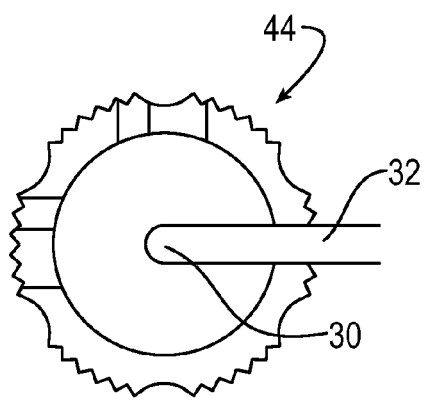

Further, with reference to FIGS. 6a1, a2, b1, c, and d, and FIGS. 7a, b, c, d, e, and f, the clamp nut 42 may include recess 52 and the sheath 44 may include a protrusion 54, or vice versa. The protrusion 54 and the recess 52 cooperate to act as a detent mechanism to hold the clamp nut in one of a locked or open position relative to the sheath. Alternatively, the protrusion 54 and the recess 52 may be formed to cooperate to act as a tongue and groove arrangement to limit the movement of the clamp nut relative to the sheath when transitioning between a locked and an open position relative to the sheath.

With additional reference now to FIG. 2, the body 20 includes the sheath 44 which defines a bore 30 and has the slot 32. At least a portion of the retainer 22 is disposed within the bore 30 with at least a portion of the bore 30a being coincident to the bore 30. In the unlocked, or open, position, retainer 22 is positioned within the sheath 44 such that slot 32a is aligned with slot 32. In the closed, or locked, position, retainer 22 is positioned within the sheath 44 such that slot 32a is unaligned with slot 32.

Figure 7E:
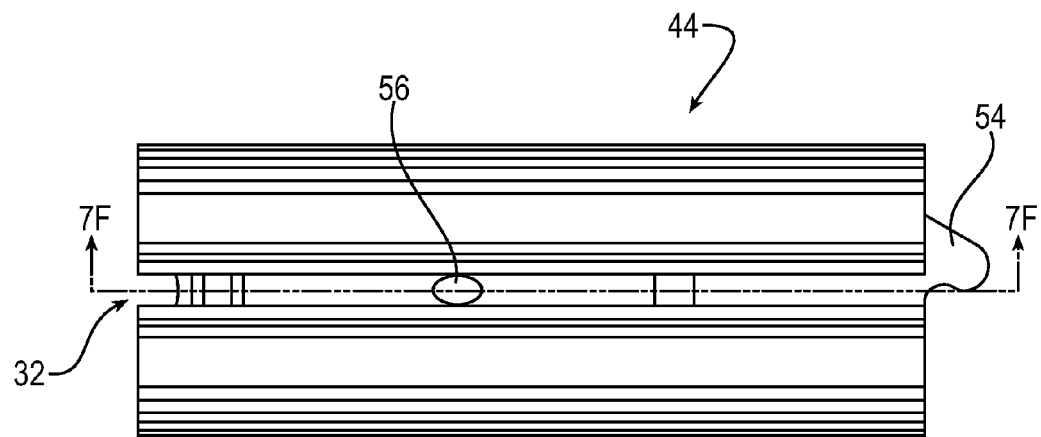
Figure 7F:
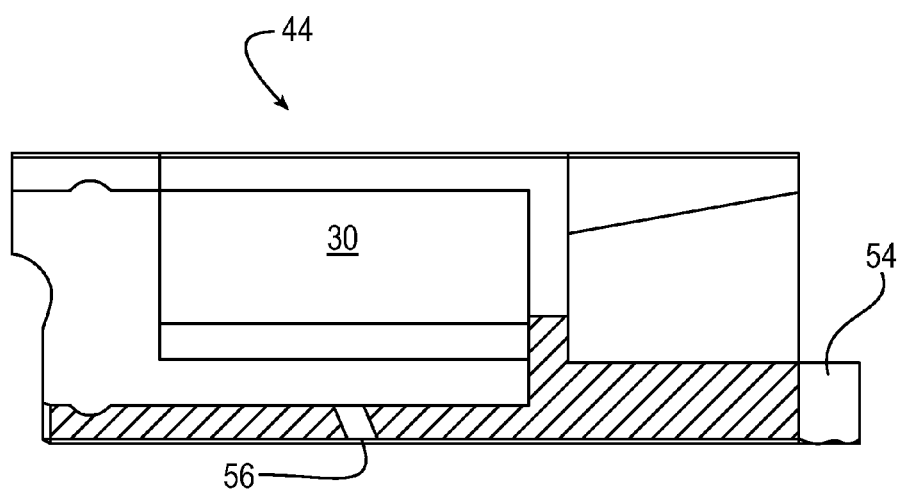

As best shown in FIGS. 7e and f, the sheath 44 may include a radially positioned aperture 56 to allow for fluid communication between the exterior of the sheath 44 and the bore 30 of the sheath. As such, during use, an operator may provide, for example, additional lubricant to a guidewire inside the sheath 44. In the case where the retainer 22 includes the pocket 50, the aperture 56 and the pocket 50 may aligned for fluid communication when in an open position such that fluid, such as a guidewire lubricant, may be placed in the pocket 50 without having to disassemble the body 20. Then the aperture 56 and the pocket 50 may be not aligned for fluid communication when in a locked position.

Returning now to FIG. 1, the guidewire positioning tool may be comprised of four parts. The sheath 44 and the collet 24 may be machined from one part, see FIGS. 4a, 4b, 4c, and 4d. The diameter of the collet 24 is smaller than the diameter of the sheath 44. The clamp nut 42 may be created separately from the sheath 44 and the collet 24, and placed over the collet 24. The clamp nut 42 is designed to engage the threads 38 and rotate around the collet 24. The clamp nut 42 is rotatable around the collet 24 and, in the illustrated embodiments, the rotation of the clamp nut 42 is stopped by the cap 40. The diameter of the clamp nut 42 is necessarily greater than the diameter of the collet 24, and preferably equal to or approximating the diameter of the sheath 44.

Figure 5A:
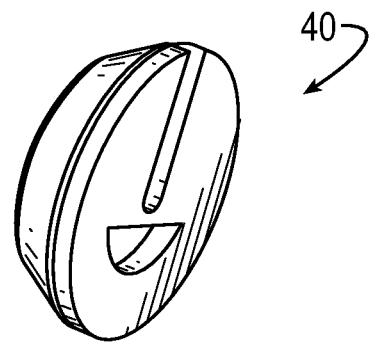
FIGS. 5a and b are a first perspective view and a second perspective view of one embodiment of the cap of the guidewire positioning tool of FIG. 1.
Figure 5B:
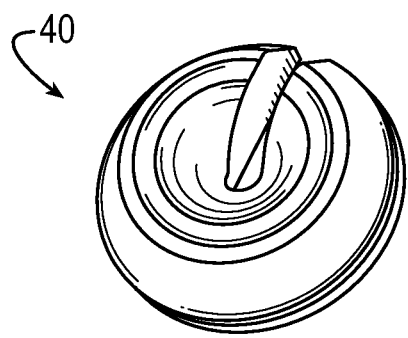

The cap 40, see FIGS. 5a and 5b, may be comprised of a separate part. The cap 40 may then be attached to the collet 24. In one embodiment, the cap 40 may be attached to the collet 24 by an adhesive. In another embodiment, the cap 40 may be attached to the collet 24 by butt welding. In still another embodiment, the cap 40 may be frictionally fit to the collet 24. The diameter of the cap 40 may be equal to or approximating the diameter of the sheath 44. In alternate embodiments of the guidewire positioning tool, the cap 40 may be optionally excluded.

The retainer 22 may be comprised of yet another separate part and attached to sheath 44. In one embodiment, the retainer 22 is frictionally fit to the sheath 44. The diameter of the retainer 22 may be equal to or approximating the diameter of the sheath 44.

As shown in FIG. 2, the diameter of the retainer 22 is designed to closely fit within the sheath 44, but still able to rotate within the sheath 44. Generally, the sheath 44 is sized to define the bore 30.

Now referring to FIGS. 3a, 3b, and 3c, and FIGS. 4a, 4b, 4c, and 4d, in still other alternate embodiments, the retainer 22 may have a protrusion or peg 45 extending from the end of the retainer 22 in the sheath 44 proximal the collet 24. The peg 45 may be configured to frictionally engage a recess or groove 25 in the sheath 44 or the collet 24. In this embodiment, the size of the groove 25 will limit the rotational movement of the sheath 44 and the retainer 22. It must be understood that this arrangement may be reversed with the protrusion on the sheath 44 and the recess on the retainer 22.

In one embodiment, the guidewire positioning tool is designed to be approximately two inches long. The outside diameter of the tool may be between 0.250"-0.3125". The diameter of the bore 30 may be between 0.020"-0.048", while the width of the slot 30 may be between 0.015"-0.043". Although a size range has been described for one embodiment of the invention, other size ranges may be used without departing from the intent of the invention. Indeed, as guidewire technology advances, the sizes of guidewires will change and so, too, will the sizes of guidewire positioning tools.

In one embodiment, the guidewire positioning tool is designed to be single-use and may be comprised of a hard plastic, for example, polyvinylchloride, acrylics, polycarbonates, or polystyrenes. In another embodiment, the guidewire positioning tool is designed to be reusable and may be comprised of a metal, for example, aluminum, stainless steel, or alloys of brass, aluminum, or stainless steel. In yet other embodiments, the guidewire positioning tool may be comprised of a mixture of plastics and metals.

It is envisioned that surgeons will use the guidewire positioning tool. However, other medical practitioners may use the guidewire positioning tool as well. For example, nurses and x-ray technicians may use the guidewire positioning tool. In alternate embodiments, the guidewire positioning tool may be used by a range of medical professionals and other users.

The guidewire positioning tool is designed to facilitate the insertion of a guidewire into patient vasculature. In one embodiment, a surgeon may mount the guidewire positioning tool laterally onto a guidewire, and may remove the guidewire positioning tool from the guidewire laterally. In this embodiment, a surgeon may easily use two or more guidewire positioning tools during the catheterization process if so desired. In an alternate embodiment, a surgeon may mount the guidewire positioning tool longitudinally onto a guidewire and may remove the guidewire positioning tool from the guidewire longitudinally.

It is envisioned a surgeon will hold the guidewire positioning tool with the proximal end oriented toward the patient's vasculature, and the distal end oriented towards his hand. However, the guidewire positioning tool may be oriented in the opposite direction without departing from the spirit of the invention.

In use, a surgeon will insert a guidewire percutaneously into a patient. The surgeon will then proceed to mount the guidewire positioning tool onto the guidewire. The surgeon will proceed to manipulate retainer 22 from the unlocked, or open, position to the closed, or locked, position to lock the guidewire within the guidewire positioning tool. In embodiments of the guidewire positioning tool which include sheath 44, movement of retainer 22 also engages sheath 44 from the unlocked, or open, position to the locked, or closed, position and serves to further lock the guidewire within the guidewire positioning tool.

As shown in FIGS. 3a, 3b, and 3c, and FIGS. 4a, 4b, 4c, and 4d, in one embodiment, the bore 30a of the retainer 22 is approximately "D" shaped, while the bore 30b of the collet 24 is approximately "U" shaped. In embodiments where a retainer 22 having the "D" shaped bore 30a rotates one quarter turn, or 90°, around the collet 24 to the closed, or locked, position, the shape of bore 30a positions and centers the guidewire proximal to the portion of the bores 30a and 30b distal from the slots 32a and 32b.

The surgeon will then proceed to feed the guidewire through the guidewire positioning tool, specifically through the bore 30 and the corresponding bores 30a and 30b. By design, the guidewire may fit loosely within bore 30. The surgeon will proceed to feed the guidewire through a patient's vasculature.

When the surgeon encounters a branch within the vasculature, the surgeon will then manipulate the collet 24 and the clamp nut 42 from the unlocked, or open, position to the locked, or closed, position. In the transition from the open to the closed position, the clamp nut 42 engages the threads 38. As clamp nut 42 twists around the collet 24, it applies pressure to the collet arms 34. As the clamp nut 42 approaches the cap 40, the amount of pressure applied to collet arms 34 increases, and the action of the clamp nut 42 causes the interstitial spaces 36 to compress. The compression of interstitial spaces 36 and the collet arms 34 decreases the diameter of bore 30b. In some embodiments, when the clamp nut 42 reaches the end of its rotation and abuts cap 40, the collet arms 34 are in tight frictional engagement with the guidewire. In other embodiments, the rotation of the clamp nut 42 is limited by the diameter of the guidewire such that the collet arms 34 are in tight frictional engagement with the guidewire before the clamp nut 42 reaches the cap 40. The pressure asserted by the collet arms 34 assists the surgeon gripping and applying force to the guidewire so he may more easily navigate the branches within the vasculature.

As shown in FIGS. 4a, 4b, 4c, and 4d, in one embodiment, the collet 24 has three collet arms 34. The collet arm 34a is larger and slightly longer than the two approximately equally sized collet arms 34b. In the unlocked, or open, position, the collet arms 34b splay outward from the bore 30b. Further, in this embodiment, the cap 40 is only attached to the collet arm 34a. In this embodiment, when the clamp nut 42 rotates around the collet 24 towards the cap 40, the movement of the clamp nut 42 along the threads 38 serves to compress the collet arms 34b relative to the collet arm 34a.

When the surgeon has selected the branch of vasculature for use and manipulated an end of the guidewire into the branch, he may twist the clamp nut 42 from the closed position to the unlocked, or open, position. The surgeon then proceeds to continue feeding guidewire through the guidewire positioning tool.

In one embodiment, the surgeon may use one hand to operate the guidewire positioning tool. In an alternate embodiment, the surgeon will use two hands to operate the guidewire positioning tool.

While principles and modes of operation have been explained and illustrated with regard to particular embodiments, it must be understood, however, that this may be practiced otherwise than as specifically explained and illustrated without departing from its spirit or scope.

What is claimed is:

1. A guidewire positioning tool, comprising:
   a sheath having a bore extending axially through a length of the sheath, the bore having a slot extending radially from the bore, the bore and slot configured to receive a guidewire;
   a collet portion extending laterally from the sheath, the collet having collet arms and interstitial spaces, a bore extending axially through a length of the collet portion, the bore having a slot extending radially from the bore, the bore and slot configured to receive a guidewire, the collet arms having threads located on the exterior of the collet arms, where when the collet portion is in an open position the collet arms extend farther from the bore at their ends distal the sheath than at their ends proximal the sheath;
   a clamp nut positioned over the collet portion and configured to threadably engage the threads, the clamp nut proximal the sheath when the collet portion is in the open position and the clamp nut distal the sheath when the collet portion is in a locked position; and
   a retainer rotatably attached to an end of the sheath opposite from the collet portion, the retainer having a bore extending axially through a length of the retainer, the bore having a slot extending radially from the bore, the bore and slot configured to receive a guidewire.

2. The guidewire positioning tool of claim 1 where the retainer includes an interior pocket for receiving fluid.

3. The guidewire positioning tool of claim 1 where one of the retainer and the sheath includes a protrusion and the other of the retainer and the sheath includes a recess where the protrusion and recess cooperate to act as a tongue and groove arrangement to limit the movement of the retainer relative to the sheath when transitioning between a locked and an open position relative to the sheath.

4. The guidewire positioning tool of claim 3 where the one of the protrusion and the recess included with the retainer is formed upon an interior end of the retainer and where the other of the protrusion and the recessed included with the sheath is formed on an interior portion of the sheath.

5. The guidewire positioning tool of claim 1 where one of the retainer and the sheath includes a protrusion and the other of the retainer and the sheath includes a recess where the protrusion and the recess cooperate to act as a detent mechanism to hold the retainer in one of a locked or open position relative to the sheath.

6. The guidewire positioning tool of claim 1 where one of the retainer and the collet includes a protrusion and the other of the retainer and the collet includes a recess where the protrusion and recess cooperate to act as a tongue and groove arrangement to limit the movement of the retainer relative to the sheath when transitioning between a locked and an open position relative to the sheath.

7. The guidewire positioning tool of claim 6 where the one of the protrusion and the recess included with the retainer is formed upon an interior end of the retainer and where the other of the protrusion and the recessed included with the collet is formed on an interior portion of the collet.

8. The guidewire positioning tool of claim 1 where one of the retainer and the collet includes a protrusion and the other of the retainer and the collet includes a recess where the protrusion and the recess cooperate to act as a detent mechanism to hold the retainer in one of a locked or open position relative to the sheath.

9. The guidewire positioning tool of claim 1 where one of the clamp nut and the sheath includes a protrusion and the other of the clamp nut and the sheath includes a recess where the protrusion and recess cooperate to act as a tongue and groove arrangement to limit the movement of the clamp nut relative to the sheath when transitioning between the locked and the open position relative to the sheath.

10. The guidewire positioning tool of claim 1 where one of the clamp nut and the sheath includes a protrusion and the other of the clamp nut and the sheath includes a recess where the protrusion and the recess cooperate to act as a detent mechanism to hold the clamp nut in one of the locked or the open position relative to the sheath.

11. The guidewire positioning tool of claim 1 where the collet portion has a cap that is distal from the sheath.

12. The guidewire positioning tool of claim 11 where the threads located on the exterior of the collet arms extend from the sheath to the cap.

13. A guidewire positioning tool, comprising:
    a sheath having a bore extending axially through a length of the sheath, the bore having a slot extending radially from the bore, the bore and slot configured to receive a guidewire;
    a collet portion extending laterally from the sheath, the collet having collet arms and interstitial spaces, a bore extending axially through a length of the collet portion, the bore having a slot extending radially from the bore, the bore and slot configured to receive a guidewire, the collet arms having threads located on the exterior of the collet arms;

a clamp nut positioned over the collet portion and configured to threadably engage the threads; and a retainer rotatably attached to an end of the sheath opposite from the collet portion, the retainer having a bore extending axially through a length of the retainer, the bore having a slot extending radially from the bore, the bore and slot configured to receive a guidewire, where the sheath includes a radially positioned aperture to allow for fluid communication between the exterior of the sheath and the bore of the sheath.

14. The guidewire positioning tool of claim 13 where the retainer includes an interior pocket for receiving fluid.

15. The guidewire positioning tool of claim 14 where the aperture and the pocket are aligned for fluid communication when in an open position and where the aperture and the pocket are not aligned for fluid communication when in a locked position.

16. The guidewire positioning tool of claim 15 where one of the retainer and the sheath includes a protrusion and the other of the retainer and the sheath includes a recess where the protrusion and the recess cooperate to act as a tongue and groove arrangement to limit the movement of the retainer relative to the sheath when transitioning between a locked and an open position relative to the sheath.

17. The guidewire positioning tool of claim 15 where one of the retainer and the sheath includes a protrusion and the other of the retainer and the sheath includes a recess where the protrusion and the recess cooperate to act as a detent mechanism to hold the retainer in one of a locked or open position relative to the sheath.

18. A guidewire positioning tool, comprising:

a sheath having a bore extending axially through a length of the sheath, the bore having a slot extending radially from the bore, the bore and slot configured to receive a guidewire;

a collet portion extending laterally from the sheath, the collet having collet arms and interstitial spaces, a bore extending axially through a length of the collet portion, the bore having a slot extending radially from the bore, the bore and slot configured to receive a guidewire, the collet arms having threads located on the exterior of the collet arms;

a clamp nut positioned over the collet portion and configured to threadably engage the threads; and a retainer rotatably attached to an end of the sheath opposite from the collet portion, the retainer having a bore extending axially through a length of the retainer, the bore having a slot extending radially from the bore, the bore and slot configured to receive a guidewire, where the clamp nut includes a visual indicator to rotatably indicate the position of the clamp nut relative to the collet portion; and wherein the visual indicator is a marker that aligns with the slot of the collet portion when in a locked position and does not align with the slot of the collet portion when in an open position.

19. The guidewire positioning tool of claim 18 where the visual indicator is a change in color about the circumference of the clamp nut.

20. The guidewire positioning tool of claim 18 where the visual indicator is a marker on the exterior of the clamp nut.

* * * * *